United States Patent [19]

Larner et al.

[11] Patent Number: 5,428,066

[45] Date of Patent: * Jun. 27, 1995

[54] METHOD OF REDUCING ELEVATED BLOOD SUGAR IN HUMANS

[76] Inventors: Joseph Larner, 1432 Grove Rd., Charlottesville, Va. 22901; Alison Kennington, 5390 Cherokee Ave., Alexandria, Va. 22312; Laura C. Huang, 3512 Marlboro Ct., Charlottesville, Va. 22901

[*] Notice: The portion of the term of this patent subsequent to Jun. 23, 2009 has been disclaimed.

[21] Appl. No.: 304,806

[22] Filed: Sep. 12, 1994

Related U.S. Application Data

[63] Continuation of Ser. No. 171,349, Dec. 20, 1993, abandoned, which is a continuation of Ser. No. 966,599, Oct. 26, 1992, abandoned, which is a continuation of Ser. No. 644,639, Jan. 23, 1991, abandoned, which is a continuation-in-part of Ser. No. 320,482, Mar. 8, 1989, abandoned.

[51] Int. Cl.$^6$ ............................................. A61K 31/045
[52] U.S. Cl. ...................................... 514/738; 514/866
[58] Field of Search ................................. 514/738, 866

[56] References Cited

U.S. PATENT DOCUMENTS

| 4,446,064 | 5/1984 | Larner | 514/103 |
|---|---|---|---|
| 4,735,936 | 4/1988 | Siren | 514/103 |
| 4,797,390 | 1/1989 | Siren | 514/103 |
| 4,801,597 | 1/1989 | Stacpoole et al. | 514/332 |
| 4,839,466 | 6/1989 | Saltiel | 530/395 |
| 4,906,468 | 3/1990 | Saltiel | 536/18.7 |
| 4,927,831 | 5/1990 | Malamas | 546/18 |
| 5,019,566 | 5/1991 | Siren | 514/103 |
| 5,023,248 | 6/1991 | Siren | 514/103 |
| 5,091,596 | 2/1992 | Kennington et al. | 568/833 |
| 5,122,603 | 6/1992 | Larner | 536/18.7 |
| 5,124,360 | 6/1992 | Larner | 514/735 |
| 5,183,764 | 2/1993 | Kennington | 436/131 |
| 5,217,959 | 6/1993 | Sabin | 514/23 |
| 5,342,832 | 8/1994 | Siren | 514/103 |

FOREIGN PATENT DOCUMENTS

| 179439 | 4/1986 | European Pat. Off. . |
|---|---|---|
| 359257 | 3/1990 | European Pat. Off. . |
| 54-138126 | 10/1979 | Japan . |
| WO90/10439 | 9/1990 | WIPO . |

OTHER PUBLICATIONS

Cecil "Textbook of Medicine" Saunders Co. p. 1059 (1983).

Price, et al., *Effect of Aldose Reductase and Resistance to Ischemic Diabetes*, Diabetes, 37(7), pp. 969–973, (Eng) 1988.

Knudsen, et al., *Myo-inositol Normalizes Decreased Sodium Permeability of the Blood-brain Barrier in Streptozotocin Diabetes*, Neuroscience (Oxford), 29(3), pp. 773–777, (Eng) 1989.

Hallman, et al., *Inositol Supplementation in Respiratory Distress Syndrome: Relationship Between Serum Concentration, Renal Excretion and Lung Effluent Phospholipids*, Pediatrics, vol. 110, No. 4, pp. 604–610, 1987.

Clements, *New Therapies for Chronic Complications of Older Diabetes Patients*, American Journal of Medicine, 80 (Supp ISA), pp. 54–60, 1986.

Holub, *The Nutritional Significance, Metabolism and Function of Myo-inositol and Phosphatidylinosital in*

(List continued on next page.)

Primary Examiner—Ceila Chang
Attorney, Agent, or Firm—Janet Sleath; William J. McNichol, Jr.

[57] ABSTRACT

A method of treating a cluster of diseases associated with elevated blood sugar levels comprising the administration of a dietary supplement of chiro-inositol. Chiro-inositol is an essential element for the synthesis of an insulin-directed mediator apparently responsible for the activation of pyruvate dehydrogenase-phosphatase. Disease conditions commonly associated with insulin-resistance, such as hypertension, lactic acidosis, obesity, coronary artery disease, and the like, are treated by administration of sufficient chiro-inositol to meet normal metabolic levels.

5 Claims, No Drawings

OTHER PUBLICATIONS

*Health and Disease,* Advanced Nutrition Research, vol. 4, pp. 107–141, 1982.

Windholz, *The Merck Index,* No. 4861, p. 722, 1983.

*Hamster Diet Inositol as Part of Vitamin Mix,* ICN Catalogue, p. AD-19, 1989.

Phillips, et al., *Cyclitols in Soybean,* J. Agric. Food Chem., 30(3) pp. 456–458, 1982.

Baumgartner, et al., *Isolation and Identification of Cyclitols in Carob Pods,* J. Agric. Food Chem., 34(5), pp. 827–829, 1986.

Williamson, et al., *Diabetes-Induced Increases in Vascular Permeability and Changes in Granulation Tissue Levels of Sorbitol, Myo-inositol, Chiroinositol, and Scyllo-inositol are Prevented by Sorbinil,* Metabolism, vol. 35, No. 4, Suppl. 1, pp. 41–45, Apr. 1986.

Narayanan, et al., *Pinitol-A New Anti-Diabetic Compound From the Leaves of Bougainvillea-Spectabilis,* Current Science, vol. 56, No. 3, pp. 139–141, (Feb. 5, 1987).

Clements, et al., *Myoinositol Metabolism in Diabetes Mellitus,* Diabetes, vol. 26, No. 3, pp. 215–221, 1977.

Larner, J. Cyclic Nucleotide Res. 8, 1982, pp. 289–296.

Niwa et al., J. Chromatography, 277, 1983, pp. 25–39.

Larner et al., Rec. Progress in Hormone Res. 38, 1982, pp. 511–556.

Cheng, et al., Diabetes, 29 1980, pp. 659–661.

Thompson, et al., Mol Cell. Biochem. 62, 1984, pp. 67–75.

Cheng, et al., J. Biol. Chem., 260(9), 1985, 5279–5285.

Messina, et al., Endocrinology 121, (4) 1987, pp. 1227–1232.

Malchoff, et al., Endocrinology, 102, (4), 1987, pp. 1327–1337.

Cheng, et al., Ann. Rev. Physiol., 47, 1985, pp. 405–424.

Suzuki, et al., J. Biol. Chem., 262(7), 1987, pp. 3199–3204.

Sato, et al., Arch. Biochem. Biophys. 260, 1988, pp. 377–387.

Greene, et al., J. Clin., Invest., 72, 1983 pp. 1058–1063.

Greene, et al., J. Clin. Invest. 55, 1975, pp. 1326–1336.

Clements, et al., Diabetes, 26(3), 1977, pp. 215–221.

Saltiel, et al., Proc. Natl. Acad. Sci. USA, 83, 1986 pp. 5793–5747.

Mato, et al., Biochem. Biophys. Res. Commun. 146(2), 1987, pp. 764–779.

Larner, et al., Biochem. Biophys. Res. Commun. 151(3), pp. 1416–1426 (1988).

Mato, et al., J. Biol. Chem., 262(5), 1987, pp. 2131–2137.

Romero, et al., Science, 240, 1988 pp. 504–511.

Kennington et al., J. Cell Biochem. Suppl. 0(13 part A), 1989 p. 142.

Sato, et al., Endocrinology, 123(3), 1988, pp. 1559–1564.

Huang, et al., FASEB, 1988, Abstract 1626.

Kennington, et al., Analytical Biochem. 181, 1989, pp. 1–5.

METHOD OF REDUCING ELEVATED BLOOD SUGAR IN HUMANS

This application is a continuation of U.S. application Ser. No. 08/171,349, filed Dec. 20, 1993, now abandoned, which is a continuation of U.S. application Ser. No. 07/966,599, filed Oct. 26, 1992, now abandoned, which is a continuation of U.S. application Ser. No. 07/644,639, filed Jan. 23, 1991, now abandoned, which in turn is a continuation-in-part of U.S. application Ser. No. 07/320,482, filed on Mar. 8, 1989, now abandoned.

FIELD OF THE INVENTION

This invention pertains to the administration of chiro-inositol for the treatment of a variety of disease conditions associated with a failure of pyruvate dehydrogenase-mediated metabolic pathways, or disease conditions otherwise linked to a failure of metabolic activation of PDH pathways, glycogen synthase pathways or other blood sugar maintenance pathways including glucose 6-phosphatase and mechanisms of insulin resistance in mammals. Specifically, chiro-inositol dietary supplements are provided for the biosynthesis of a chiro-inositol containing insulin mediator capable of stimulating PDH and glycogen synthase and inhibiting glucose 6-phosphatase and thus overcoming insulin resistance, lowering blood sugar and lowering elevated lactic acid.

BACKGROUND OF THE INVENTION

In parent application Ser. No. 320,482, filed Mar. 8, 1989, the inventors reported the identification of a high correlation between insulin-resistant diabetic disease states and an absence from the urine of D-chiro-inositol. This correlation led to the observation that insulin resistance may be due to an individual's inability to synthesize chiro-inositol, leading to an inability to form a specific insulin mediator, apparently responsible for the activation of the pyruvate dehydrogenase complex, and in particular, pyruvate dehydrogenase phosphatase, or PDH-P. The mediator also activates glycogen synthase (GS) by activating in particular glycogen synthase phosphatase or GS-P. It also may inhibit glucose 6-phosphatase. Thus, the administration of D-chiro-inositol, as a dietary supplement, is demonstrated and claimed in that parent application as an effective treatment for insulin-resistant diabetics and lowering blood sugar. Other copending applications are directed to the mediator itself, as well as a method of screening individuals for diabetic conditions, involving assaying body fluids, including urine and serum, for the presence of chiro-inositol.

It has been widely reported that insulin resistance, which is characterized by the manifestation of non-insulin-dependent diabetes mellitus (NIDDM) is frequently associated with hypertension, coronary artery disease (arteriosclerosis) lactic acidosis and obesity, as well as related disease states. These disease states are associated with a cluster of risk factors, including hyperinsulinemia, high plasma triglyceride concentration, low HDL cholesterol concentration, and other risk factors traditionally associated with coronary artery disease (CAD). Although a variety of possible genetic and treatment methodologies have been proposed, the fundamental connection between these disease states, and a method of treating that fundamental problem remains elusive.

Accordingly, it remains an object of those of skill in the art to establish a fundamental understanding of the relationship between the above-identified disease states, and a method of treating the same.

SUMMARY OF THE INVENTION

Applicants have now determined that the insulin mediator incorporating chiro-inositol is apparently responsible for the activation of at least one or both of the glycogen synthase metabolic pathway and the pyruvate dehydrogenase complex, specifically, activation of pyruvate dehydrogenase-phosphatase or PDH-P as well as a glycogen synthase phosphatase or GS-P. It also inhibits glucose 6-phosphatase. While applicants do not wish to be bound by this theory, it appears that the chiro-inositol containing insulin mediator, for which chiro-inositol is necessary, activates PDH-P, thus initiating the conversion of phosphorylated inactive PDH to dephosphorylated or active PDH, which is responsible, among other things, for oxidative glucose metabolism. This mediator also activates GS-P thus initiating the conversion of phosphorylated inactive GS to dephosphorylated active GS responsible among other things for non-oxidative glucose metabolism. It also inhibits glucose 6-phosphatase, the enzyme responsible for increasing blood sugar. Thus, individuals exhibiting low levels of chiro-inositol, whether due to an inability to synthesize chiro-inositol, a relatively high removal rate of chiro-inositol, or a failure to absorb chiro-inositol, will characteristically exhibit a failure of the PDH complex, central to oxidative glucose metabolism, and particularly, the conversion of pyruvate to oxidative acetyl Co-A. It further appears that the mediator may also be involved in the glycogen synthase side of the metabolic pathway. Specifically, the action of glycogen synthase phosphatase may be inhibited by the absence of the mediator central to non-oxidative glucose metabolism; namely, glycogen storage. A third step in glucose production, namely, glucose 6-phosphatase may also be sensitive to inhibition by the mediator. Thus, in the absence of the mediator, glucose will be produced by the liver.

This failure may be partial or complete. Clearly, a failure of the body's glucose metabolism is directly implicated in a wide variety of the disease states associated, on a statistical basis, with insulin-resistance, including obesity, and a predisposition to coronary artery disease. Similarly, lactic acidosis implicates at least a partial failure of the PDH complex. An active PDH complex would lower lactic acid levels. Hypertension and its associated insulin resistance may be directly related to a failure of the PDH complex, although the specific pathway remains unclear.

Accordingly, a failure of the PDH complex or of the GS complex, or of the glucose 6-phosphatase due to a low level or absence of chiro-inositol mediator (referred to as insulin mediator in the parent application), caused by a failure of chiro-inositol synthesis, may be treated by administration of a dietary supplement of chiro-inositol. High levels of chiro-inositol may lead to synthesis of the insulin mediator, allowing a restoration of "normal" insulin direction of PDH complex and GS complex activity and glucose 6-phosphatase activity pathways, through the role of this critical mediator.

DETAILED DESCRIPTION OF THE INVENTION

The invention comprises the administration of chiro-inositol to individuals suffering from disease conditions related to a partial or complete failure of the PDH complex, glycogen synthase pathway or related blood sugar level maintenance mechanisms including glucose 6-phosphatase, owing to a low level or absence of chiro-inositol necessary for the synthesis of the insulin mediator responsible for the activation of PDH-P and GS-P and inhibition of glucose 6-phosphatase or additional unknown mechanisms involving chiro-inositol. Thus, administration of chiro-inositol, through a variety of pathways, makes possible the synthesis of this essential mediator, alleviating the disease condition by treating its source, rather than symptomatic treatment as is generally prescribed in the art. The net result is a substantial reduction of hallmark elevated blood sugar levels. Of course, treatment by the administration of chiro-inositol, according to the claimed invention, may be accompanied by symptomatic treatment, to the extent such remains appropriate.

The essential, non-dietary carbohydrate that is the focus of this invention, chiro-inositol, is related to myo-inositol, the structures of the various optically active compounds being set forth herein below.

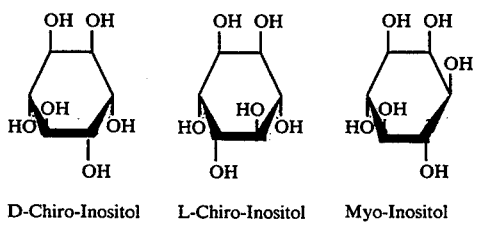

D-Chiro-Inositol    L-Chiro-Inositol    Myo-Inositol chiro-inositol is available from non-dietary sources, in forms that may not be readily assimilated by the body. Thus, the methylester of chiro-inositol is found in sugar pine hardwood (*PINUS LAMBERTIANA* DOUGL) (Anderson, AB 1953 *Ind. Eng. Chem.* 45, 593–596). Various esterified forms can also be isolated from legumes (Schweizer, T. F., Horman, I., Wuersch, P, 1978, *J. Sci. Food Agric.*, 29, pages 148–154. However, the assimilatable sugar itself is not believed to appear, in sufficient quantities, in normal dietary foods, to make up for a lack of the ability to synthesize the sugar. This inability may prevent the formation of the chiro-inositol containing insulin mediator responsible for the activation of PDH-P, GS-P or other suitable pathways for lowering blood sugar including glucose 6-phosphatase.

The provision of a dietary supplement, in vitamin amounts, to provide an in vivo therapeutic level of chiro-inositol, overcomes this deficiency. Administration of chiro-inositol to those identified, through an appropriate screening test, as exhibiting low levels of chiro-inositol, may be employed to achieve the goals of this invention. A suitable screening test is set forth in U.S. application Ser. No. 476,953, filed Feb. 8, 1990, the entire content of which is incorporated by reference. Similarly, those exhibiting clinical symptoms of the identified disease states, to the extent they are dependent on the absence of the mediators, may be treated by simple administration of the dietary supplement.

As noted above, chiro-inositol can be isolated from natural sources through purification and deesterification reactions. It can also be synthesized directly from myo-inositol, commonly available, by direct inversion of the hydroxyl on the three position.

In the general population, and those not likely to develop the elevated blood sugar-related disease states addressed herein, chiro-inositol is not present in substantial concentrations. Accordingly, the dietary supplement need be present only in vitamin-like concentrations to provide an adequate means of intervening in clinical conditions, as well as preventing the onset of clinical symptoms in those predisposed to their development. In general, dosage values will range from 250 to 5000 milligrams, and may be achieved through a variety of pathways. An alternative dosage formulation would be administered in the range of 3.5–300 mg/kg, preferably 3.5–70 mg/kg of body weight, more preferably 5–20 mg/kg. Adequacy of dosage levels may be determined by assaying patient urine or serum levels for chiro-inositol. Urinary levels below about 1.0 $\mu$g/ml, or serum levels below about 0.1 $\mu$g/ml, are indicative of chiro-inositol insufficiency. As noted above, the carbohydrate is directly absorbed, and thus may be most conveniently administered orally. Other forms of administration are also suitable.

The active agent, chiro-inositol, may be administered alone, or together with other actives. The actives may be combined, by oral administration, with additives chosen from the group consisting of sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g. lecithin), a condensation product of an alkylene oxide with a fatty acid (e.g., polyoxyethylene stearate), a condensation product of ethylene oxide with a long chain aliphatic alcohol (e.g., haptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservative such as ethyl or n-propyl p-hydroxybenzoate, one or more coloring agent, one or more flavoring agent, and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for the preparation of an aqueous suspension by the addition of water provide the active ingredient in admixture with a dispersing or wetting agent, a suspending agent, and one or more preservative. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol. Among the acceptable vehicles and solvents that may be employed are water.

Derivatives of chiro-inositol designed to increase absorption and cellular transfer may include fatty acid short or long chain esters or ethers, succinates, diacyiglycerol derivatives, esters of lactic or pyruvic acid or amino acid or peptide ester derivatives or other derivatives to be defined on the basis of biological activity in vivo to lower blood sugar levels.

There are no known toxic or deleterious side effects from the administration of chiro-inositol. Due to the very low concentrations at which therapeutic levels are achieved, the chiro-inositol can be administered to virtually all those diagnosed either exhibiting clinical symptoms of elevated blood sugar-related hypertension, obesity, coronary artery disease, lactic acidosis, and obesity in combination with insulin-resistant diabetes, or genetically predisposed to the development, through the screening test discussed above. Thus, the dietary additive addressed herein may be administered to infants over the age of one year, and all others at risk or exhibiting clinical symptoms. Under the age of one year, it is believed that the digestive system may be insufficiently developed to achieve positive results through the addition of the dietary supplement.

The invention disclosed above has been described with regard to specific examples, dosage levels, carriers and additives. Within the scope of the claims appended hereto, other formats, variations and combinations will occur to those of ordinary skill in the art, without the exercise of inventive skill. Such alterations do not depart from the invention, except as provided in the claims appended hereto.

What is claimed is:

1. A method for the treatment of insulin resistance comprising administering an effective amount of D-chiro-inositol.

2. The method of claim 1 wherein D-chiro-inositol is administered orally.

3. The method of claim 1 wherein D-chiro-inositol is administered in amounts of 3.5 mg/kg to 300 mg/kg.

4. The method of claim 1 wherein D-chiro-inositol is administered in amounts of 5 mg/kg to 20 mg/kg.

5. A pharmaceutical composition containing an anti-insulin resistance effective amount of D-chiro-inositol admixed with a pharmaceutically acceptable carrier.

* * * * *